United States Patent

Kozak

[11] 4,041,949
[45] Aug. 16, 1977

[54] FLEXIBLE WAISTBAND DIAPER

[75] Inventor: Theodore Frederick Kozak, Manchester, Conn.

[73] Assignee: Union Carbide Corporation, New York, N.Y.

[21] Appl. No.: 702,211

[22] Filed: July 2, 1976

[51] Int. Cl.² ........................................... A61F 13/16
[52] U.S. Cl. ................................... 128/287; 128/290 R
[58] Field of Search .................. 128/284, 287, 290 R, 128/286, 296

[56] References Cited

U.S. PATENT DOCUMENTS

| | | | |
|---|---|---|---|
| 3,828,784 | 8/1974 | Zoephel | 128/287 |
| 3,886,941 | 6/1975 | Duane | 128/287 |
| 3,890,973 | 6/1975 | Davis | 128/286 |
| 3,924,626 | 12/1975 | Lee et al. | 128/287 |
| 3,929,135 | 12/1975 | Thompson | 128/287 |
| 3,930,501 | 1/1976 | Schaar | 128/287 |

Primary Examiner—Aldrich F. Medbery
Attorney, Agent, or Firm—Clement J. Vicari

[57] ABSTRACT

A disposable diaper having a stretchable waistband having a topsheet provided with means for passing liquid therethrough, a water impermeable backsheet and an absorbent pad disposed therebetween, one of said topsheet or backsheet being fabricated from a water impermeable stretchable plastic film having end portions extending beyond said absorbent pad, each end portion being folded upon itself and adhered to itself to form a stretchable waistband for the diaper.

18 Claims, 5 Drawing Figures

FLEXIBLE WAISTBAND DIAPER

This invention relates to disposable diapers and more particularly relates to a disposable diaper which is provided with a stretchable waistband formed from either the topsheet or backsheet of the disposable diaper.

The use of disposable diapers has greatly increased in recent years due to their ease of use, low cost and the obvious sanitary value of having a clean, fresh, disposable diaper for use without the inconvenience of having to wash and reuse a previously used nondisposable diaper.

In its most fundamental construction a disposable diaper merely comprises a layer of disposable absorbent material lining a backing sheet of liquid impermeable material which may be disposable or reusable. The thickness of the layer of absorbent material can be varied depending upon the desired use. For example, if the diaper were to be used overnight for an older baby it would be required to have a greater absorptive capacity than one used for a short time during the day or for an infant and consequently the absorbent layer would be thicker. The length and width of the diaper can also be varied for different size babies. Generally, the absorbent pad will be about ⅛ to ½ inch thick and the diaper will have a length of about 12 to 18 inches and a width of about 8 to 16 inches.

While a baby diaper constructed in this manner supplies the essential ingredients of a disposable diaper, namely an absorbent layer and a liquid impermeable backing sheet, modifications have previously been proposed to overcome one or more of the defects inherent in the basic construction. It was found, for example, that when the absorbent layer became soaked with urine it tended to wad together or lost most of its integral strength and began to shred.

In order to overcome these disadvantages it has been common to place a layer of non-woven gauze, or other material which will maintain its integrity after wetting on top of the absorbent layer of the diaper thereby sandwiching the absorbent layer between a topsheet of self-supporting but liquid permeable material and a backing sheet of liquid impermeable material. Such a construction overcame the disadvantages of shredding but tended to make the baby uncomfortable after wetting since the urine would partially be absorbed by the topsheet which was against the skin of the baby. This contact of the baby's skin with urine on the surface of the diaper is one of the principal causes of diaper-derived skin rash. Additionally, upon removal of a wet diaper, it was found that the baby's skin was wet and drying was necessary before a clean diaper could be applied.

In an attempt to overcome this deficiency it has been suggested that the topsheet be made hydrophobic or water-shedding to maintain the layer which is in contact with the baby's skin as dry as possible. One recognized approach has been to form the topsheet of the diaper in part or completely of hydrophobic fibers or by coating or impregnating an otherwise hydrophilic topsheet with a hydrophobic resin.

In another recognized approach, a film of plastic has been utilized as the topsheet of the diaper with provision being made for the passage of liquid through the plastic topsheet into the absorbent pad.

Thus according to U.S. Pat. No. 3,814,101 issued June 4, 1974, the plastic topsheet for the disposable diaper described therein is provided with valvular openings for passage of liquid therethrough to the absorbent core. U.S. Pat. No. 3,221,738 issued to G. E. Eckberg et al on Dec. 7, 1965 discloses as topsheet for a disposable diaper, a thin plastic foil which is heat treated in such a way that the liquid insulating property of the foil is completely or partially neutralized, so that liquid reaching the heat-treated foil surface is automatically sucked in through the foil and absorbed by the core. More recently U.S. Pat. No. 3,929,135 issued to Hugh Ansley Thompson on Dec. 30, 1975 provides a plastic topsheet for a disposable diaper having tapered capillaries of specific design and construction and which is adapted to pass liquid therethrough into an absorbent layer disposed subjacent to the topsheet.

It has been the custom to secure these disposable diapers on an infant by utilizing a pressure sensitive tape fastener which has been disposed on the backsheet of the diaper in an area overlying the absorbent pad. When the disposable diaper is placed on an infant the tape fastener is secured to either abutting or overlapping corners of the diaper so as to provide as secure a fit as possible around the waist of an infant. Since the waist size of infants can vary appreciably it has heretofore been difficult to provide a proper fit for the diaper which would be both comfortable to the infant while at the same time providing safeguards against leakage through the top of the diaper particularly when the infant is in a prone position.

This is because of the construction of conventional diapers which have not afforded any appreciable expansive properties when tapes were fastened to the diapers and applied to the infant. Neither tape nor waist construction of conventional diapers has any significant "give" or resiliency and in fact efforts have been made to make the tape fastener and the area accommodating the tape fastener relatively strong and relatively ungiving. This unyielding characteristic makes it difficult to maintain good fit during the rigors of usage.

According to the present invention it has been found that the above disadvantages can be either eliminated or reduced significantly by appropriate selection of materials of specific construction for the topsheet and backsheet coupled with appropriate positioning of the tape fasteners on a disposable diaper.

Accordingly it is an object of the present invention to provide a disposable diaper having a stretchable waistband.

A further object of the invention is to provide a topsheet and backsheet for a disposable diaper at least one of which is stretchable and extends beyond the absorbent pad and which when folded upon itself forms a waistband for the diaper.

A further object is to provide a disposable diaper in which the waistband of the diaper can be stretched to a greater degree than the body or core of the diaper which accommodates the absorbent material therein, without disturbing the integrity of the diaper.

These and other objects will be apparent from the following description taken in conjunction with the accompanying drawings in which:

FIG. 1 is a perspective view of a diaper with a portion cut away to reveal details of construction, the diaper having a backsheet and a topsheet and wherein the topsheet is fabricated from a stretchable plastic material as defined herein and which is provided with openings for passage of liquid and showing the topsheet extending beyond the longitudinal edges of the absorbent pad to form end portions which are to be folded upon themselves to form a waistband for the diaper.

Broadly contemplated, the present invention provides a disposable diaper having a stretchable waistband comprising in combination a topsheet for placement adjacent to the body and being provided with means for passing liquid therethrough, a water impermeable backsheet and an absorbent pad disposed between said topsheet and backsheet, one of said topsheet or backsheet being fabricated from a water impermeable stretchable plastic film having a Young's Modulus of less than 5000 lbs/in$^2$ and which exhibits recovery characteristics such that at up to 20% elongation it will recover about 99% and from 20 to 50% elongation it will recover from 99 to 90%, respectively, and still maintain a force of 0.05 lbs, said stretchable plastic film having end portions extending beyond said absorbent pad, each end portion being folded upon itself and adhered to itself to form a stretchable waistband for the diaper. Fastening means are also provided for securing the diaper on an infant such as a pair of pressure sensitive tape fasteners, each having a fixed end segment secured to a corner of the waistband of the diaper on one of the end portions of the diaper.

The invention can be practiced on any conventional type disposable diaper which utilizes either a stretchable plastic backsheet or a stretchable (as defined herein) plastic topsheet provided with openings, illustrations of which were indicated previously. The topsheet and backsheet are separate sheets which accommodate the absorbent therebetween and which can be adhered around their periphery as disclosed in U.S. Pat. No. 3,814,101. According to one embodiment of the invention the disposable diaper has a hydrophobic liquid impermeable backsheet and a stretchable water impermeable plastic topsheet provided with means for permitting liquid to pass therethrough. The topsheet extends beyond the edges of the absorbent pad and is folded upon itself and adhered to provide a waistband for the diaper. According to this embodiment the topsheet is a plastic film and the preferred means for permitting passage of liquid therethrough are as disclosed in U.S. Pat. No. 3,814,101. Most preferably the topsheet also includes the dimples disclosed in said patent.

According to another embodiment of the invention, the disposable diaper has a stretchable liquid impermeable backsheet which extend beyond the longitudinal edges of the absorbent pad to form end portions and each end portion is folded upon itself to provide a waistband for the diaper. The topsheet is a porous non-woven material and can be composed in part or completely of hydrophobic fibers. Alternatively the topsheet can be hydrophilic and treated with a hydrophobic resin such as by coating or impregnating the otherwise hydrophilic topsheet with the hydrophobic resin.

Figure 1:
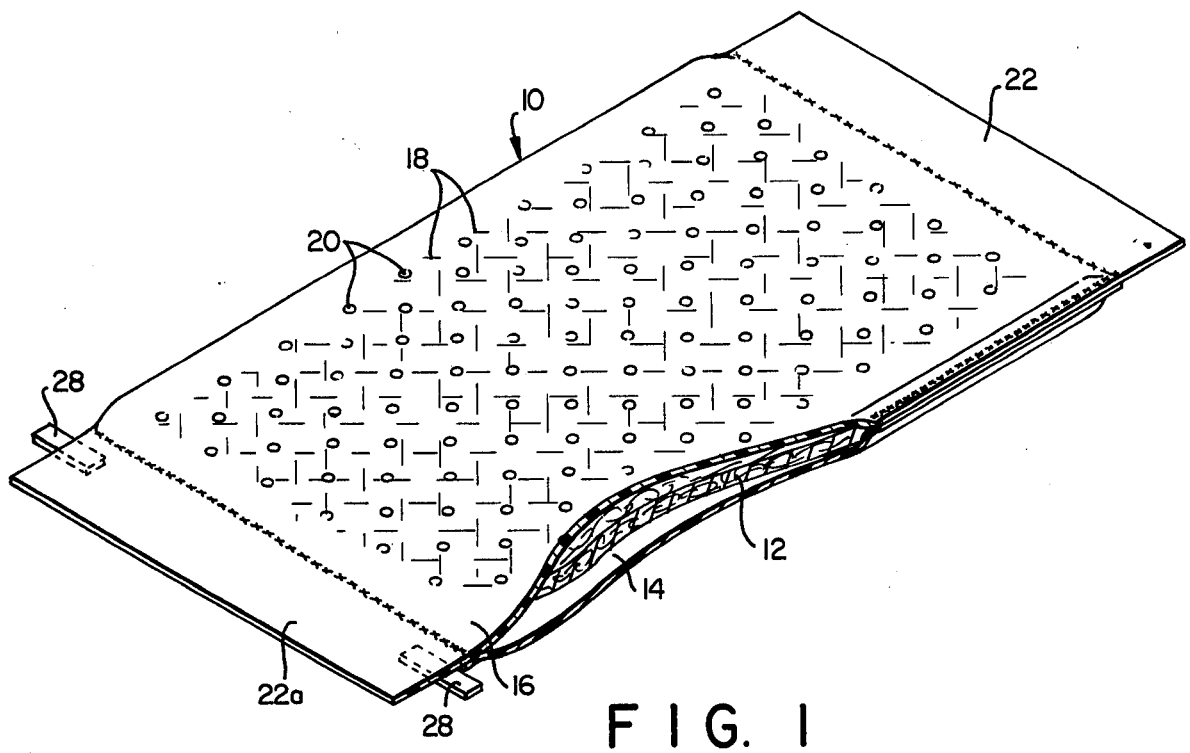
Figure 2:
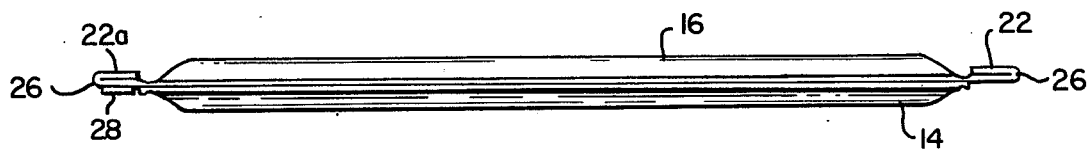
FIG. 2 is a side view of the diaper of FIG. 1 but showing the end portions of the topsheet folded upon themselves to form a waistband for the diaper.

For a clearer understanding of the invention reference is made to FIGS. 1 and 2 which illustrate the preferred embodiment of the invention and wherein reference numeral 10 generally designates the disposable diaper of the instant invention.

The diaper 10 includes a rectangular absorbent pad 12 substantially centrally located and sandwiched between a thin, flexible backsheet 14 of liquid impermeable material such as polyethylene film and a thin stretchable plastic topsheet 16 also of a normally liquid impermeable material. Topsheet 16 is provided with means for passing liquid to the absorbent pad such as is disclosed in U.S. Pat. No. 3,221,738 or U.S. Pat. No. 3,929,135. Preferably however, topsheet 16 has a plurality of slits 18 and can include a system of dimples 20 as disclosed in U.S. Pat. No. 3,814,101 which slits and dimples will be described in greater detail hereinafter.

The absorbent pad 12 can be a plurality of layers of absorbent tissue paper or wadding stacked to the desired thickness. The wadding layers need not be adhered to each other but, since it has been common practice to adhesively, mechanically, or otherwise secure the layers to each other to maintain the relative position of the layers and the shape of the absorbent pad, such can also be done in the disposable diaper of the present invention. The wadding can be stacked to form a pad of any desired thickness and hence absorbency can be controlled for any particular use.

Absorbent materials other than tissue and wadding will of course be useful in the diaper construction of the present invention. For example, absorbent non-woven pads can be fabricated to any desired thickness and substituted for the absorbent pads described above. One such absorbent pad which has been used extensively in disposable diapers is a wood pulp product commonly known as wood fluff and is prepared in the same manner as a non-woven fabric. Thus such type absorbent pad is also useful as the absorbent pads of the inserts of the present invention.

The only criteria for utility in the present invention are that the material be absorbent, be capable of being fabricated in the form of a pad, be compatible with the waste products with which it will come in contact and be non-irritating to the skin.

In the copending application of Theodore F. Kozak and Paul Mohr, Ser. No. 702,212 filed concurrently herewith and assigned to a common assignee, there is disclosed a stretchable plastic film material suitable for use as an outer covering for a disposable diaper.

The stretchable plastic films disclosed therein are suitable for use in the present invention and therefore the disclosure of copending application Ser. No. 702,212 is incorporated herein by reference.

Briefly however, the plastic stretchable film contemplated for use in the present invention is limited to those materials possessing the required strength and stretchability. The material should be thin, flexible, self-supporting, and substantially a water impermeable sheet of film.

It is essential that the stretchable plastic film contemplated for use in the present invention be one having the requisite stress to strain properties as determined at any specified point.

Thus the film must have a stretch (Young's) Modulus less than 5000 lbs/in$^2$, preferably from 300 to 4000 lbs/in$^2$ and most preferably from 350 to 1000 lbs/in$^2$, and must also exhibit recovery such that at up to 20% elongation it will recover 99% and from 20 to 50% elongation it will recover from 99% to 90% and still maintain a force of not less than 0.05 lbs, preferably not less than 0.3 lbs.

Examples of stretchable hydrophobic films having the requisite properties include films of ethylene-ethyl acrylate, having the requisite ethylacrylate content, ethylene vinyl acetate, polyvinyl chloride, and films made from polyester urethanes such as "Estane" 5710 resin available from B. F. Goodrich Co.

Films fabricated from polyethylene would not be suitable since they do not meet the above criteria. However copolymers of ethylene could be suitable provided the polymer content is controlled so as to conform to the above criteria.

As shown in FIG. 1, topsheet 16 extends longitudinally beyond the absorbent pad 12 to form end portions 22 and 22a.

These end portions each extend longitudinally beyond absorbent pad 12 and transversely across the diaper 10. As shown in FIG. 2, each of end portions 22 and 22a is folded upon itself. The superimposed layers of topsheet in the fold region are adhered to each other by any suitable manner such as by heat sealing. As will be seen from FIG. 2, the folded end portions 22 and 22a extend longitudinally beyond the absorbent pad 12 and define waistband 26 of the diaper. The waistband 26 extends from absorbent pad 12 a distance sufficient to accommodate a pair of tape fasteners 28 on the corners 30 and 30a of waistband 26, (although it will be obvious that the tape fastener can alternately be positioned on the other corners of the waistband. It will be seen that where the tape fasteners 28 are positioned on corners 30 and 30a that the area is free of absorbent pad material and indeed the entire waistband 26 is free of absorbent pad material.

Although the topsheet is shown folded once upon itself to form the waistband, the number of folds can be greater such as two folds or even three folds provided however that enough waistband is provided to accommodate tape fasteners on the corners as explained previously.

Conventionally, it has been the practice to adhere the absorbent pad to the backsheet or topsheet. Thus under conventional techniques when the tape fastener was secured to the backsheet it was positioned overlying the absorbent material. Exerting pressure on the tape fastener to accommodate a large waist size infant resulted in tearing of the backsheet and/or separation of the absorbent material due to the non-yieldability of the structure.

According to the present invention the tape fasteners are positioned on the waistband 26 so that the fixed end portion has no absorbent material underlying the tape fastener. Since the topsheet is stretchable, and since the waistband is an extension of the topsheet body material, pressure can be exerted on the tape fastener when mounting the diaper on the infant so that the greatest amount of stress is placed on the waistband portion of the diaper which has a higher permissible degree of stretchability than the topsheet overlying the absorbent material. This is because the topsheet overlying the absorbent material is normally adhered to the absorbent material to prevent migration of the absorbent material.

One film which has been found particularly useful as the topsheet is an ethylene-ethyl acrylate film having the requisite characteristics described herein. The film should have a thickness of from about 0.4 to about 2.0 mils with about 1.0 to 1.5 mils being preferred.

As described above, the topsheet 16 is made from substantially liquid impermeable plastic film material and is provided with valvular openings or slits 18 on the portion overlying the absorbent pad 12 and is also optionally provided with dimples 20.

The valvular openings or slits and the dimples on the top surface of the diaper are of a construction and frequency as disclosed in U.S. Pat. No. 3,803,101. Briefly however, and as disclosed in the above mentioned patent, the term "valvular" as used throughout the specification and in the claims is intended to refer to apertures in the top surface which are capable of opening to permit passage of liquid under certain circumstances and reclosing to retard passage of liquid under certain other circumstances. When open, the valvular openings should have the ability to pass at least 20 milliliters of liquid within 10 seconds when an area of about 20 square inches is wetted.

The slits according to the preferred embodiment of the present invention must be substantially straight since, if they are curved, V-shaped or of any other configuration, they will form flaps in the surface of the film which are too easily opened and tend to remain open. Since slits, while permitting sufficient passage of liquid in the direction of the absorbent pad, do not act to substantially reduce backflow of liquid. This disadvantage is also present if holes are formed in the film by removing pieces of film material as opposed to puncturing the film without removal of film material. The film is thereby left open to the uncontrolled passage of liquid in both directions.

FIG. 1 shows a preferred arrangement of slits. The slits 18 are arranged in longitudinal rows in a manner such that each row constitutes a longitudinal array of substantially parallel straight slits each angularly disposed with respect to the longitudinal axis of the row. Adjacent rows are similarly disposed except that the slits are arranged in a manner such that the end points of each slit lie in a line substantially between the end points of corresponding slits in the adjacent alternate rows. The slits should each be from about 30 to about 150 slits per square inch, each of such slits being from about 0.07 to about 0.2 inch in length. The most preferred film contains about 81 slits per square inch, each about 0.1 inch in length.

The dimples 20 are distributed across the topsheet 16 of the diaper 10 in the manner shown in FIG. 1. The topsheet 16 contains a plurality of dimples arranged in staggered parallel rows and which extend beyond the plane of the top surface of the diaper. The configuration of these dimples can be circular, eliptical, rectangular, diamond shaped, and the like, the important criteria being that they be formed in a manner such that there is substantially no breaking or cutting of the topsheet during or after fabrication.

It is important that during fabrication of the dimples on the top surface of the diaper that they not be cut, or melted to an extent which would hinder the controlled passage of liquid to the absorbent pad (which as explained previously, is the function of the valvular openings). It will be evident that if cutting or breaking of either top surface occurs during fabrication of the dimples, that the liquid will pass through these cuts or breaks when the absorbent pad is unsaturated and once the absorbent pad is saturated or even partially saturated, that these entry points will also serve as points or sites through which the liquid exudes back through the topsheet in contact with, for example, a baby's skin.

For these reasons and furthermore in view of the ease and simplicity of fabrication, I have found that the preferred form of the dimple is circular as shown in FIG. 1.

The dimples can be formed in the topsheet 16 in a variety of ways. The easiest and therefore the most preferred method involves the use of a roller equipped with heating means and having a number of spikes or probes extending therefrom across the width of the roller and around its circumference. The spikes, pins, or probes, which have smooth, rounded end points, can be spaced as desired on the roller in order to provide the desired number of dimples to the diaper. The dimples are provided on the topsheet 16 of the diaper preferably after the valvular openings, and this operation can be effected by passing the diaper containing the valvular openings in contact with the heated roller. In this technique, the diaper is supported on a resilient back-up member, such as an endless conveyor belt, or a resilient back-up roller. The depth of the dimple can be controlled by limiting the depth to which the probes depress the film. If desired, portions of the topsheet 16 can be retained in its untreated (without the dimples) condition. This can be accomplished, for example, along a strip about one inch wide near the periphery of the topsheet. Since the topsheet is thermoplastic, the amount of heat and pressure applied to the areas to be treated should be strictly controlled in order to avoid substantially puncturing the material. As a general rule, the amount of heat required should be enough to soften the film, and the amount of pressure should be sufficient to plastically distort the film to the general contour of the probe. It will, of course, be understood that the correct heat and pressure conditions will depend (among other variables) upon the residence time of the treated absorbent pad, i.e., the length of time the topsheet is in contact with the roller, the thickness of the absorbent pad, etc. The correct conditions, however, can be easily ascertained by one skilled in the art and hence no further detailed description of the conditions appears necessary.

The dimples can be arranged on the topsheet 16 in a variety of patterns. Thus, the overall design effect can be diamond shaped, curvilinear, herringbone and the like. The preferred design configuration is a system of substantially straight staggered, parallel rows along the top surface of the overwrap. The number of dimples per square inch of absorbent pad area can be varied over a relatively wide range.

The advantages and wicking characteristics of the dimple slit combination are fully described in the U.S. Pat. No. 3,814,101 issued to Theodore Fredrick Kozak on June 4, 1974 who is the inventor of the subject matter herein.

According to the preferred embodiment shown in FIGS. 1 and 2, the backsheet 14 as mentioned previously is of a liquid impermeable material and is preferably a film of thermoplastic material which is thin, flexible and self-supporting.

The backsheet is preferably an olefinic or vinyl film. Polyethylene of a thickness of from about 0.4 to about 1.5 mils is most preferred. This type of film has previously been used extensively for this purpose and commonly has had an embossed design in its surface to simulate the appearance and hand of cloth. These manufacturing techniques will also find use in the diaper of the present invention. The assembly of the diaper follows, more or less, conventional methods of fabrication. The topsheet and backsheet are cut to approximately the same dimensions except that the topsheet is of a longer length to provide for the subsequent overlapping. The size can be varied according to the desired use, for example in an infant's diaper a size of 10 × 14 inches for the backsheet 10 × 18 for the topsheet might be sufficient whereas in a diaper for a large child a size of 12 × 16 inches for the backsheet and 12 × 20 for the topsheet would be better and a size of 14 × 18 inches for the backsheet and 14 × 22 for the topsheet might be preferred for a diaper which could accommodate a toddler.

The topsheet and backsheet are juxtaposed one on the other with the absorbent pad sandwiched therebetween in approximately the center of the sheets. The absorbent pad should be of a length and width slightly smaller than the backsheet to permit sealing of the topsheet to the backsheet around their periphery. An overhang of about ½ inch on each side should be sufficient. Sealing can conveniently be accomplished by heat sealing the edges.

In addition, the heat seal which joins the topsheet to the backsheet adjacent the longitudinal ends of the pad (the edges extending across the width of the diaper) can advantageously also join the folded over topsheet forming the waistband of the diaper.

Figure 3:
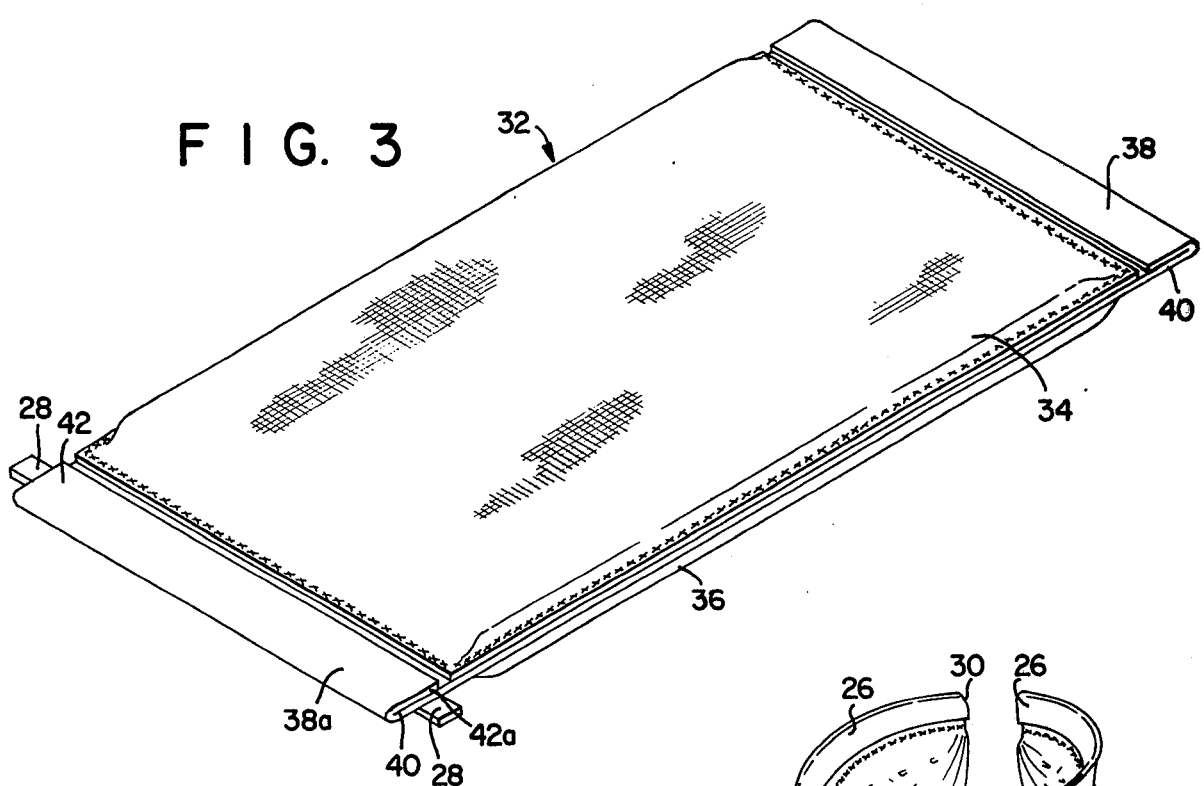
FIG. 3 is a perspective view of another embodiment of a disposable diaper having a porous non-woven topsheet and wherein the backsheet is stretchable and extends beyond the longitudinal edges of the absorbent pad and which is folded upon itself to form a waistband for the disposable diaper.

According to another embodiment of the invention, illustrated in FIG. 3 where like parts are indicated by like reference numbers, the stretchable waistband is formed from the backsheet of the disposable diaper. Thus referring to FIG. 3 the diaper 32 includes the absorbent pad sandwiched between a liquid permeable topsheet 34 and a thin stretchable plastic backsheet 36 of liquid impermeable material.

Topsheet 34 can be a porous non-woven material and can be composed in part or completely of hydrophobic fibers. Alternatively, the topsheet can be hydrophilic and treated with a hydrophobic resin such as by coating or impregnating the otherwise hydrophilic topsheet with the hydrophobic resin. The backsheet 36 is constructed of the same materials as the topsheet 16 of the preferred embodiment of diaper 10 shown in FIGS. 1 and 2 and has end portions 38 and 38a which are each folded upon themselves to form waistband 40.

Fastening means are disposed on the corner portions 42 and 42a of the waistband 40 to secure the diaper to the infant. The fastening means are preferably tape fasteners 28 which as shown in FIG. 3 are positioned on the corners 42 and 42a of waistband 40.

Although the fastening means illustrated in both embodiments are tape fasteners, it will be obvious that other conventional fastening means known to the art can be utilized.

The type of tape fastener which can be utilized is conventional in the art and in general contains a fixed end segment which is permanently affixed to the diaper and a releasable end segment having some form of adhesion on its surface and which is adapted to be adhesively secured to opposing corners of the diaper.

The materials used in the fabrication of the tape fastener of the present invention are not limited to any particular chemical composition since it is their physical properties rather than their chemical properties which are important according to the invention. These materials should, of course, be less flexible than the materials of the overwrap and should be self-supporting.

Merely as illustrative, the pressure sensitive tape fasteners disclosed in U.S. Pat. Nos. 3,853,129 and 3,874,386 issued Dec. 10, 1974 and Apr. 1, 1975 respectively can be utilized.

Figure 4:
FIG. 4 is a view of the disposable diaper of FIG. 1 showing the position of the tape fastener in nonoperating position, that is, not affixed to opposing corners of the formed waistband of the diaper.
Figure 5:
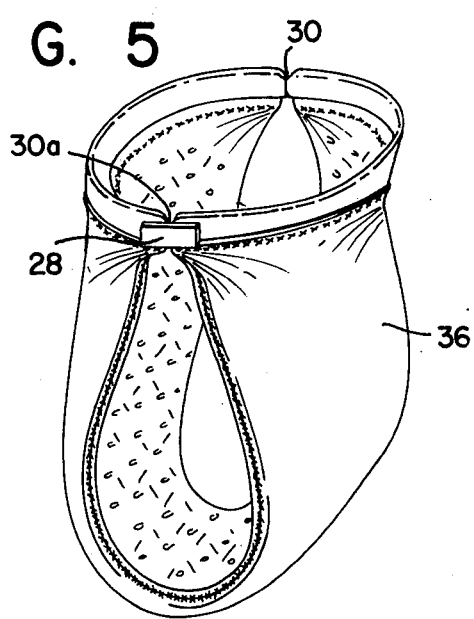
FIG. 5 is a view of the diaper of FIG. 1 showing the tape fastener in operating position on an infant (not shown) and illustrating the stretching of the waistband of the diaper.

FIG. 4 illustrates the disposable diaper of the first embodiment in non-operating position on an infant (not shown) whereas FIG. 5 shows the same diaper in operating position wherein the waistband 26 is stretched and secured by tape fasteners 28 to provide a tight fit around the infant.

It will be seen from FIG. 5 that the waistband is stretched and that the topsheet 16 overlying absorbent pad 12 of the diaper is substantially unaffected.

It will be obvious that while the present invention has been set forth in some detail and described with particularity it is susceptible to changes, modifications and alterations without departing from the scope and spirit of the invention as defined in the appended claims.

What is claimed is:

1. A disposable diaper having a stretchable waistband comprising in combination a topsheet for placement adjacent to the body and being provided with means for passing liquid therethrough, a water impermeable backsheet and an absorbent pad disposed between said topsheet and backsheet, one of said topsheet or backsheet being fabricated from a water impermeable stretchable plastic film having a Young's Modulus of less than 5000 lbs/in$^2$ and which exhibits recovery characteristics such that at up to 20% elongation it will recover about 99% and from 20 to 50% elongation it will recover from 99 to 90%, respectively, and still maintain a force of 0.05 lbs, means for providing an expansible waist portion for the diaper comprising said stretchable plastic film having end portions extending beyond the longitudinal end of said absorbent pad, each end portion being folded upon itself and adhered to itself to form a stretchable waistband for the diaper, and a pair of laterally and oppositely extending fastening means disposed on said waistband for securing said diaper on an infant.

2. A disposable diaper according to claim 1 wherein said fastening means are pressure sensitive tape fasteners each having a fixed end and a releasable end and wherein said fixed end is secured to a corner of said waistband of the diaper on one of the folded end portions.

3. A disposable diaper according to claim 2 wherein said topsheet is fabricated from said plastic film material and wherein said backsheet is fabricated from said non-stretchable material.

4. A disposable diaper according to claim 3 wherein said backsheet is a polyethylene film.

5. A disposable diaper according to claim 4 wherein said means for passing liquid through said topsheet are valvular openings and wherein said topsheet also includes a system of dimples extending across the surface of said topsheet.

6. A disposable diaper according to claim 1 wherein said plastic film has a Young's Modulus of from 300 to 4000 lbs/in$^2$.

7. A disposable diaper according to claim 1 wherein said plastic film has a Young's Modulus of from 350 to 1000 lbs/in$^2$.

8. A disposable diaper according to claim 7 wherein said plastic film is an ethylene-ethyl acrylate film.

9. A disposable diaper according to claim 3 wherein each end portion of said topsheet has a plurality of folds defining said waistband.

10. A disposable diaper according to claim 3 wherein said backsheet terminates immediately after said absorbent pad in the diaper length direction and wherein said topsheet is adhered to said backsheet immediately adjacent said absorbent pad.

11. A disposable diaper according to claim 2 herein said backsheet is fabricated from said plastic film material and wherein said topsheet is fabricated from said non-stretchable material.

12. A disposable diaper according to claim 11 wherein said topsheet is a polyethylene film.

13. A disposable diaper according to claim 11 wherein said topsheet is fabricated from non-woven cloth.

14. A disposable diaper according to claim 11 wherein said plastic film has a Young's Modulus of from 300 to 4000 lbs/in$^2$.

15. A disposable diaper according to claim 11 wherein said plastic film has a Young's Modulus of from 350 to 1000 lbs/in$^2$.

16. A disposable diaper according to claim 11 wherein said plastic film is an ethylene-ethyl acrylate film.

17. A disposable diaper according to claim 11 wherein each end portion of said backsheet has a plurality of folds defining said waistband.

18. A disposable diaper according to claim 11 wherein said topsheet terminates immediately after said absorbent pad in the diaper length direction and wherein said backsheet is adhered to said topsheet immediately adjacent said adsorbent pad.

* * * * *